(12) United States Patent
Yoneda et al.

(10) Patent No.: US 8,242,169 B2
(45) Date of Patent: Aug. 14, 2012

(54) EMULSION COMPOSITION

(75) Inventors: Tadashi Yoneda, Chiba (JP); Naoko Ito, Chiba (JP); Kazuo Furuya, Chiba (JP)

(73) Assignee: Showa Denko K.K., Tokyo (JP)

( * ) Notice: Subject to any disclaimer, the term of this patent is extended or adjusted under 35 U.S.C. 154(b) by 795 days.

(21) Appl. No.: 12/307,166

(22) PCT Filed: Jul. 3, 2007

(86) PCT No.: PCT/JP2007/063623
§ 371 (c)(1), (2), (4) Date: Dec. 31, 2008

(87) PCT Pub. No.: WO2008/004685
PCT Pub. Date: Jan. 10, 2008

(65) Prior Publication Data
US 2009/0252773 A1 Oct. 8, 2009

(30) Foreign Application Priority Data
Jul. 4, 2006 (JP) .................................. 2006-184748

(51) Int. Cl.
*A61K 31/375* (2006.01)
*C07D 307/62* (2006.01)
(52) U.S. Cl. ........................................ 514/474; 549/315
(58) Field of Classification Search ................ 514/474; 548/477; 549/315
See application file for complete search history.

(56) References Cited

U.S. PATENT DOCUMENTS
2007/0128146 A1 * 6/2007 Fujino et al. ............... 424/70.31

FOREIGN PATENT DOCUMENTS

| JP | 2000-256173 A | 9/2000 |
|---|---|---|
| JP | 2005-187465 A | 7/2005 |
| JP | 2005-187466 A | 7/2005 |
| JP | 2005187465 A * | 7/2005 |
| WO | 02/078650 A1 | 10/2002 |
| WO | 03/086384 A1 | 10/2003 |
| WO | 2005/051334 A1 | 6/2005 |
| WO | WO 2005051334 A1 * | 6/2005 |
| WO | 2006/033476 A1 | 3/2006 |

OTHER PUBLICATIONS

Machine Translation of JP 2005-187465 obtained from http://dossier1.ipdl.inpit.go.jp on Nov. 1, 2011.*
CAPLUS Record of JP 2005-187465 by Eiko et al., 2005.*

* cited by examiner

*Primary Examiner* — Joseph Kosack
*Assistant Examiner* — Matthew Coughlin
(74) *Attorney, Agent, or Firm* — Sughrue Mion, PLLC

(57) ABSTRACT

An emulsion composition of the present invention includes (A) a salt of a higher fatty acid ester of ascorbic acid-2-phosphoric acid ester, (B) a polyglycerin fatty acid monoester including polyglycerin having a mean polymerization degree of 8 to 12 and an unsaturated fatty acid residual group of 14 to 22 carbon atoms, (C) a polyglycerin fatty acid monoester comprising polyglycerin having a mean polymerization degree of 2 to 6 and an unsaturated fatty acid residual group of 14 to 22 carbon atoms, and (D) a hydrocarbon oil, wherein the blending ratio by mass between the component (B) and the component (C) is in the range of 1:1 to 3:1, and the blending ratio by mass between the total of the components (B) and (C) and the component (D) is in the range of 10:1 to 1:4. By the use of the emulsion composition of the present invention, a skin external preparation can be provided which is prevented from decrease of a salt of a higher fatty acid ester of ascorbic acid-2-phosphoric acid ester attributable to decomposition of the salt, is excellent in retention of moisture, and has a beautiful appearance.

11 Claims, No Drawings

EMULSION COMPOSITION

TECHNICAL FIELD

The present invention relates to an emulsion composition comprising a salt of a higher fatty acid ester of ascorbic acid-2-phosphoric acid ester and having excellent stability, a skin external preparation comprising the composition and a cosmetic comprising the composition. The invention also relates to a method for stabilizing the skin external preparation containing the salt of ascorbic acid derivative.

BACKGROUND ART

Ascorbic acid and its derivatives are known as compounds exhibiting efficacy and effects in whitening action, anti-oxidant action, collagen synthesis promotion action, etc., and they are added to medicines, cosmetics, feeds and the like.

Of the ascorbic acid derivatives, compounds wherein a hydroxyl group at the 2-position is esterified with phosphoric acid and a hydroxyl group at the 6-position is esterified with a higher fatty acid and their salts are hardly oxidized and are stable and amphipathic. On that account, these compounds have high affinity for living organisms and rapidly penetrate into the organism tissues such as the skin, so that application of the compounds to medicines, cosmetics, feeds, etc. is expected.

However, when skin external preparations are prepared from the salts of higher fatty acid esters of ascorbic acid-2-phosphoric acid ester, decomposition of the salts takes place in the preparations, and there occurs a problem that their effects are not sufficiently obtained.

As means to obtain a stable emulsion, an emulsified cosmetic comprising an ascorbic acid-phosphoric acid ester salt, a specific surface active agent and an oil agent has been disclosed in the past in, for example, a patent document 1, and an emulsified cosmetic comprising specific two kinds of polyglycerin fatty acid esters, lecithin and an oil component has been disclosed in the past in, for example, a patent document 2.

In any of the means disclosed in the above documents, however, it is difficult to stably emulsify the salt of a higher fatty acid ester of ascorbic acid-2-phosphoric acid ester.

Further, the present inventors have already proposed a skin external preparation and a cosmetic each of which comprises a salt of a higher fatty acid ester of ascorbic acid-2-phosphoric acid ester, an oil component, a surface active agent, water and a higher alcohol and has excellent stability (patent document 3).

The cosmetic of the patent document 3, however, is white, and any cosmetic having a transparent to translucent beautiful appearance has not been obtained yet.

Patent document 1: Japanese Patent Laid-Open Publication No. 256173/2000
Patent document 2: WO 2002/078650
Patent document 3: Japanese Patent Laid-Open Publication No. 187465/2005

DISCLOSURE OF INVENTION

It is an object of the present invention to provide a skin external preparation, which is prevented from decrease of a salt of a higher fatty acid ester of ascorbic acid-2-phosphoric acid ester attributable to decomposition of the salt, is excellent in retention of moisture and has a beautiful appearance.

It is another object of the present invention to provide, through provision of such a skin external preparation as above, a method for stabilizing the above skin external preparation comprising a salt of a higher fatty acid ester of ascorbic acid-2-phosphoric acid ester.

The present inventors have earnestly studied, and as a result, they have found that the above objects are attained by using a specific polyglycerin fatty acid monoester as an emulsifying agent and a specific oil component in a specific blending ratio. Based on the finding, the present invention has been accomplished.

That is to say, the present invention relates to the following matters.

[1] An emulsion composition comprising:
(A) a salt of a higher fatty acid ester of ascorbic acid-2-phosphoric acid ester, said higher fatty acid ester of ascorbic acid-2-phosphoric acid ester being represented by the following formula (1):

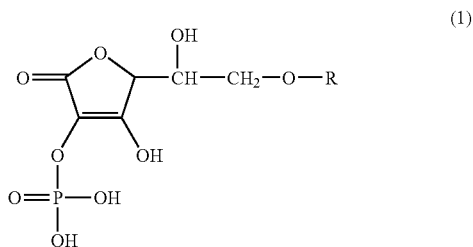

wherein R is a higher fatty acid residual group,
(B) a polyglycerin fatty acid monoester comprising polyglycerin having a mean polymerization degree of 8 to 12 and an unsaturated fatty acid residual group of 14 to 22 carbon atoms,
(C) a polyglycerin fatty acid monoester comprising polyglycerin having a mean polymerization degree of 2 to 6 and an unsaturated fatty acid residual group of 14 to 22 carbon atoms, and
(D) a hydrocarbon oil,
wherein the blending ratio by mass between the component (B) and the component (C), (B):(C), is in the range of 1:1 to 3:1, and the blending ratio by mass between the total of the components (B) and (C) and the component (D), (B)+(C): (D), is in the range of 10:1 to 1:4.

[2] The emulsion composition as stated in [1], wherein R in the formula (I) is a residual group of an aliphatic carboxylic acid of 10 to 20 carbon atoms.

[3] The emulsion composition as stated in [2], wherein the aliphatic carboxylic acid is lauric acid, myristic acid, palmitic acid, stearic acid, 2-hexyldecanoic acid or isostearic acid.

[4] The emulsion composition as stated in [2], wherein the aliphatic carboxylic acid is palmitic acid.

[5] The emulsion composition as stated in [2], wherein the aliphatic carboxylic acid is 2-hexyldecanoic acid.

[6] The emulsion composition as stated in [1], wherein the component (A) is a Na salt, a K salt, a Mg salt or a Zn salt.

[7] The emulsion composition as stated in any one of [1] to [6], wherein the content of the component (A) is in the range of 0.01 to 20% by mass.

[8] The emulsion composition as stated in [1], wherein the component (B) is polyglyceryl-10 oleate, the component (C) is polyglyceryl-2 oleate, and the component (D) is squalane or liquid paraffin.

[9] The emulsion composition as stated in [1], wherein the mean emulsion particle diameter is in the range of 1 nm to 200 nm.

[10] A skin external preparation, comprising the emulsion composition of any one of [1] to [9].

[11] A cosmetic comprising the emulsion composition of any one of [1] to [9].

[12] A method for stabilizing the skin external preparation of [10], comprising preparing an emulsion having a mean emulsion particle diameter of 1 nm to 200 nm by using, as emulsifying agents, (B) a polyglycerin fatty acid monoester comprising polyglycerin having a mean polymerization degree of 8 to 12 and an unsaturated fatty acid residual group of 14 to 22 carbon atoms and (C) a polyglycerin fatty acid monoester comprising polyglycerin having a mean polymerization degree of 2 to 6 and an unsaturated fatty acid residual group of 14 to 22 carbon atoms.

The emulsion composition of the present invention hardly suffers decrease of the salt of a higher fatty acid ester of ascorbic acid-2-phosphoric acid ester attributable to decomposition of the salt and retains a transparent to translucent beautiful appearance for a long period of time. Therefore, the emulsion composition is useful for all use applications of skin external preparations and is particularly useful for cosmetics.

BEST MODE FOR CARRYING OUT THE INVENTION

The emulsion composition, the skin external preparation comprising the composition, the cosmetic comprising the composition and the method for stabilizing the skin external preparation according to the invention are described in detail hereinafter.

[Emulsion Composition]

The emulsion composition of the invention comprises (A) a salt of a higher fatty acid ester of ascorbic acid-2-phosphoric acid ester, (B) a polyglycerin fatty acid monoester comprising polyglycerin having a mean polymerization degree of 8 to 12 and an unsaturated fatty acid residual group of 14 to 22 carbon atoms, (C) a polyglycerin fatty acid monoester comprising polyglycerin having a mean polymerization degree of 2 to 6 and an unsaturated fatty acid residual group of 14 to 22 carbon atoms, and (D) a hydrocarbon oil.

<Component (A)>

The higher fatty acid ester of ascorbic acid-2-phosphoric acid ester, that becomes a main body of the salt of a higher fatty acid ester of ascorbic acid-2-phosphoric acid ester (A) (said higher fatty acid ester of ascorbic acid-2-phosphoric acid ester being also referred to as "ascorbic acid ester" hereinafter) for use in the invention, is a compound represented by the following formula (1).

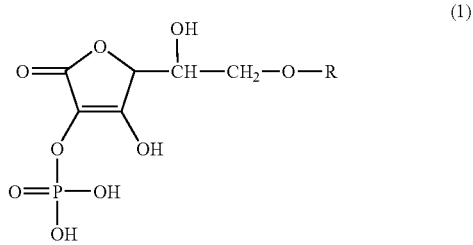

In the formula (1), R is a higher fatty acid residual group, namely, an acyl group derived from a higher fatty acid. Preferred examples of the higher fatty acids include aliphatic carboxylic acids of 10 to 20 carbon atoms, such as lauric acid, myristic acid, palmitic acid, stearic acid, 2-hexyldecanoic acid and isostearic acid. Of these, palmitic acid and 2-hexyldecanoic acid are more preferable.

The salt of ascorbic acid ester (A) for use in the invention is preferably a compound wherein a phosphoric acid residual group that constitutes a phosphoric acid ester linkage at the 2-position and a base form a salt.

Examples of the salts of ascorbic acid ester (A) include a Na salt, a K salt, a Ca salt, a Mg salt and a Zn salt. Of these, a Na salt is more preferable. The salts of ascorbic acid ester (A) may be used singly or in combination of two or more kinds.

The content of the salt of ascorbic acid ester (A) in the emulsion composition of the invention is usually in the range of 0.01 to 20% by mass, preferably 0.1 to 10% by mass, more preferably 0.5 to 5% by mass. When the content is in this range, the emulsion composition rapidly penetrates into the skin and can exert efficacy and effects as a skin external preparation, so that such a content is preferable.

<Component (B) and Component (C)>

The polyglycerin fatty acid monoester (B) for use in the invention is an ester type emulsifying agent comprising polyglycerin having a mean polymerization degree of 8 to 12 and an unsaturated fatty acid residual group of 14 to 22 carbon atoms, and is specifically polyglyceryl-10 oleate or the like.

The polyglycerin fatty acid monoester (C) for use in the invention is an ester type emulsifying agent comprising polyglycerin having a mean polymerization degree of 2 to 6 and an unsaturated fatty acid residual group of 14 to 22 carbon atoms, and is specifically polyglyceryl-2 oleate or the like.

In the present invention, the blending ratio by mass between the component (B) and the component (C) needs to be in the range of 1:1 to 3:1, and is preferably in the range of 1.5:1 to 2.5:1. If the blending ratio is out of the above range, an emulsion having a transparent to translucent appearance is not obtained occasionally.

The component (B) and the component (C) are each used in an amount of usually 0.05 to 5% by mass, preferably 0.1 to 3% by mass, more preferably 0.2 to 2% by mass, in the whole amount of the emulsion composition.

<Component (D)>

The hydrocarbon oil (D) for use in the invention is a kind of oil agent usually used for skin external preparations such as cosmetics, and examples of such hydrocarbon oils include ozokerite, α-olefin oligomer, light isoparaffin, light liquid isoparaffin, squalene, squalane, synthetic squalane, vegetable squalane, ceresin, paraffin, polyethylene powder, polybutene, microcrystalline wax, liquid isoparaffin, liquid paraffin, mineral oil and vaseline. Of these, liquid paraffin and squalane are preferable.

In the present invention, the blending ratio by mass between the total of the components (B) and (C) and the component (D) needs to be in the range of 10:1 to 1:4, and is preferably in the range of 5:1 to 1:2. If the blending ratio is higher than 10:1, an emulsion having a transparent to translucent appearance is not obtained occasionally. On the other hand, if the blending ratio is lower than 1:4, satisfactory stability is not obtained occasionally.

<Features of Emulsion Composition and Process for Preparing Emulsion Composition>

The emulsion composition of the invention has a transparent to translucent appearance. The expression "transparent to translucent appearance" used herein means that letters of a newspaper placed on the other side of a transparent cell having a cell length of 5 mm and containing the emulsion composition are distinguishable through the cell.

The emulsion composition having such a transparent to translucent appearance is obtained by allowing the composition to have a mean emulsion particle diameter of not more than 200 nm, preferably 1 nm to 200 nm. When the mean emulsion particle diameter is in this range, the emulsion composition has high transparency and excellent appearance, so that such a mean emulsion particle diameter is preferable. The mean emulsion particle diameter can be measured by the use of a commercially available particle size distribution measuring device, such as "Nanotrack UPA-EX150" manufactured by Nikkiso Co., Ltd.

Examples of emulsification methods to obtain such an emulsion composition include surface chemical methods, such as phase inversion temperature emulsification method, agglomeration method, liquid crystal emulsification method, D phase emulsification method and self-emulsification method, and mechanical methods, such as methods using high-pressure emulsifier, high-shearing dispersing machine and colloid mill. Of these, the self-emulsification method is particularly preferable because a desired emulsion composition is obtained by low-speed stirring only.

<Other Components>

To the emulsion composition of the invention, common components that are generally used for skin external preparations may be added within limits not detrimental to the effects of the invention. Such components can be added in amounts of, for example, 0.01 to 25 parts by mass based on the total 100 parts by mass of the components (A) to (D). Examples of such components include the following substances:

natural waxes, such as jojoba oil, carnauba wax, candelilla wax, rice bran wax, shellac, lanolin, mink sebaceous wax, spermaceti wax, sugarcane wax, sperm whale oil, beeswax and montan wax, natural fats and fatty oils, such as avocado oil, almond oil, olive oil, extra virgin olive oil, sesame seed oil, rice bran oil, rice oil, rice germ oil, corn oil, safflower oil, soybean oil, maize oil, rape seed oil, persic oil, palm kernel oil, palm oil, castor oil, sunflower oil, high oleic sunflower oil, grape seed oil, cotton seed oil, coconut oil, hydrogenated coconut oil, beef tallow, hydrogenated oil, horse oil, mink oil, yolk oil, yolk fat oil, rose hip oil, kukui nut oil, evening primrose oil, wheat germ oil, peanut oil, Camellia jeponica oil, Camellia kissi oil, cacao butter, Japanwax, beefbone tallow, nest's-foot oil, swine tallow, equine tallow, ovine tallow, shea butter, *macadamia* nut oil and meadowfoam seed oil;

fatty acids, such as lauric acid, myristic acid, palmitic acid, stearic acid, behenic acid, oleic acid, linoleic acid, linolenic acid, γ-linolenic acid, isostearic acid, 12-hydroxystearic acid, undecylenic acid and coconut oil fatty acid;

higher alcohols, such as isostearyl alcohol, octyl dodecanol, hexyl decanol, cholesterol, phytosterol, lauryl alcohol, myristyl alcohol, cetyl alcohol, stearyl alcohol, oleyl alcohol, behenyl alcohol and cetostearyl alcohol;

alkylglyceryl ethers, such as batyl alcohol, chimyl alcohol, serachyl alcohol and isostearyl glyceryl ether;

esters, such as isopropyl myristate, butyl myristate, isopropyl palmitate, ethyl stearate, butyl stearate, ethyl oleate, ethyl linoleate, isopropyl linoleate, cetyl caprylate, hexyl laurate, isooctyl myristate, decyl myristate, myristyl myristate, cetyl myristate, octadecyl myristate, cetyl palmitate, stearyl stearate, decyl oleate, oleyl oleate, cetyl ricinoleate, isostearyl laurate, isotridecyl myristate, isocetyl myristate, isostearyl myristate, octyldodecyl myristate, 2-ethylhexyl palmitate, isocetyl palmitate, isostearyl palmitate, 2-ethylhexyl stearate, isocetyl stearate, isodecyl oleate, octyldodecyl oleate, octyldodecyl ricinoleate, ethyl isostearate, isopropyl isostearate, cetyl 2-ethylhexanoate, cetostearyl 2-ethylhexanoate, stearyl 2-ethylhexanoate, hexyl isostearate, ethylene glycol dioctanoate, ethylene glycol dioleate, propylene glycol dicaprylate, propylene glycol dicaprylate/dicaprate, propylene glycol dicaprate, propylene glycol dioleate, neopentyl glycol dicaprate, neopentyl glycol dioctanoate, glyceryl tricaprylate, glyceryl tri 2-ethyl hexanoate, glyceryl tricaprylate/tricaprate, glyceryl tricaprylate/tricaprate/tristearate, glyceryl triundecylate, glyceryl triisopalmitate, glyceryl triisostearate, trimethylolpropane tri 2-ethylhexanoate, trimethylolpropane triisostearate, pentaerythrityl tetra 2-ethylhexanoate, pentaerythrityl tetramyristate, pentaerythrityl tetraisostearate, diglyceryl tetraisostearate, octyldodecyl neopentanotae, isocetyl octanoate, isostearyl octanoate, 2-ethylhexyl isopelargonate, hexyldecyl dimethyloctanoate, octyldodecyl dimethyloctanoate, 2-ethylhexyl isopalmitate, isocetyl isostearate, isostearyl isostearate, octyldodecyl isostearate, lauryl lactate, myristyl lactate, cetyl lactate, octyldodecyl lactate, triethyl citrate, acetyltriethyl citrate, acetyltributyl citrate, trioctyl citrate, triisocetyl citrate, trioctyldodecyl citrate, diisostearyl malate, 2-ethylhexyl hydroxystearate, di 2-ethylhexyl succinate, diisopropyl adipate, diisobutyl adipate, dioctyl adipate, diheptylundecyl adipate, diethyl sebacate, diisopropyl sebacate, dioctyl sebacate, cholesteryl stearate, cholesteryl isostearate, cholesteryl hydroxystearate, cholesteryl oleate, dihydrocholesteryl oleate, phytosteryl isostearate, phytosteryl oleate, isocetyl 12-stearoyl hydroxystearate, stearyl 12-stearoyl hydroxystearate, isostearyl 12-stearoyl hydroxystearate, polyoxyethylene (3) polyoxypropylene (1) cetyl ether acetate, polyoxyethylene (3) polyoxypropylene (1) isocetyl ether acetate, isononyl isononanoate, octyl isononanoate, tridecyl isononanoate and isotridecyl isononanoate;

silicone oils, such as methyl polysiloxane, methylphenyl polysiloxane, methyl hydrogen polysiloxane, methyl cyclopolysiloxane, octamethyl cyclotetrasiloxane, decamethyl cyclopentasiloxane, dodecamethyl cyclohexasiloxane, octamethyl trisiloxane, decamethyl tetrasiloxane, tetradecamethyl hexasiloxane, highly polymerized methyl polysiloxane, dimethylsiloxane-methyl(polyoxyethylene)siloxane-methyl(polyoxypropylene)siloxane copolymer, dimethylsiloxane-methyl(polyoxyethylene)siloxane copolymer, dimethylsiloxane-methyl(polyoxypropylene)siloxane copolymer, dimethylsiloxane-methylcetyl oxysiloxane copolymer, dimethylsiloxane-methyl stearoxysiloxane copolymer, polyether modified silicone, alcohol modified silicone, alkyl modified silicone and amino modified silicone;

polymers, such as sodium alginate, carrageen, agar, furcellaran, guar gum, quince seed, Amorphophalus konjak (arum root) mannan, tamarindgum, taragum, dextrin, starch, locustbean gum, gum arabic, gum gatti, karaya gum, gum tragacanth, arabinogalactan, pectin, quince, chitosan, starch, curdlan, xanthan gum, gellan gum, cyclodextrin, dextran, pullulan, microcrystalline cellulose, methyl cellulose, ethyl cellulose, hydroxyethyl cellulose, hydroxypropyl cellulose, hydroxypropylmethyl cellulose, carboxymethyl cellulose, carboxy starch, cationized cellulose, starch phosphate ester, cationized guar gum, carboxymethyl-hydroxypropylated guar gum, hydroxypropylated guar gum, albumin, casein, gelatin, sodium polyacrylate, polyacrylic amide, carboxyvinyl polymer, polyethylene imine, highly polymerized polyethylene glycol, polyvinyl alcohol, polyvinyl pyrrolidone, polyvinyl ether, polyacrylamide, acrylic acid copolymer, methacrylic acid copolymer, maleic acid copolymer, vinylpyridine copolymer, ethylene/acrylic acid copolymer, vinyl pyrrolidone based polymer, vinyl alcohol/vinyl pyrrolidone copolymer, nitrogen-substituted acrylamide based polymer, amino modified silicone, cationized polymer, dimethylacryl ammonium based polymer, acrylic acid based anion polymer, methacrylic acid based anion polymer, modified silicone, acrylate/methacrylate alkyl (C 10 to 30) copolymer and polyoxyethylene/polyoxypropylene copolymer;

alcohols, such as ethanol, isopropyl alcohol, 1-butanol, 2-butanol and benzyl alcohol;

dihydric alcohols, such as ethylene glycol, propylene glycol, 1,3-butanediol, 3-methyl-1,3-butanediol, 1,2-pentanediol, 1,2-hexanediol, diethylene glycol, triethylene glycol, polyethylene glycol, dipropylene glycol and polypropylene glycol;

trihydric alcohols, such as glycerin;

ethers of trihydric alcohols, such as diglycerin and polyglycerin;

sugar alcohols, such as mannitol, sorbitol, xylitol, maltitol, erythritol and pentaerythritol;

monosaccharides, such as glucose, fructose and xylose;

oligosaccharides, such as sucrose, lactose, maltose and trehalose;

anionic surfactants, such as coconut oil fatty acid potassium, coconut oil fatty acid sodium, coconut oil fatty acid triethanolamine, potassium laurate, sodium laurate, triethanolamine laurate, potassium myristate, sodium myristate, isopropanolamine myristate, potassium palmitate, sodium palmitate, isopropanolamine palmitate, potassium stearate, sodium stearate, triethanolamine stearate, potassium oleate, sodium oleate, castor oil fatty acid sodium, zinc undecylenate, zinc laurate, zincmyristate, magnesiummyristate, zinc palmitate, zinc stearate, calcium stearate, magnesium stearate, aluminum stearate, calcium myristate, magnesium myristate, aluminum dimyristate, aluminum isostearate, polyoxyethylene lauryl ether acetate, sodium polyoxyethylene lauryl ether acetate, polyoxyethylene tridecyl ether acetate, sodium polyoxyethylene tridecyl ether acetate, sodium stearoyl lactate, sodium isostearoyl lactate, sodium lauroyl sarcosine, coconut oil fatty acid sarcosine, sodium coconut oil fatty acid sarcosine, coconut oil fatty acid sarcosine triethanolamine, lauroyl sarcosine, potassium lauroyl sarcosine, lauroyl sarcosine triethanolamine, oleoyl sarcosine, sodium myristoyl sarcosine, sodium stearoyl glutamate, coconut oil fatty acid acyl glutamic acid, potassium coconut oil fatty acid acyl glutamate, sodium coconut oil fatty acid acyl glutamate, coconut oil fatty acid acyl glutamate triethanolamine, lauroylacyl glutamic acid, potassium lauroylacyl glutamate, sodium lauroylacyl glutamate, lauroylacyl glutamate triethanolamine, myristoylacyl glutamic acid, potassium myristoylacyl glutamate, sodium myristoylacyl glutamate, stearoylacyl glutamic acid, potassium stearoylacyl glutamate, disodium stearoylacyl glutamate, sodium hydrogenated beef tallow fatty acid acyl glutamate, sodium coconut oil fatty acid/hydrogenated beef tallow fatty acid acyl glutamate, sodium coconut oil fatty acid methylalanine, lauroyl methylalanine, sodium lauroyl methylalanine, lauroyl methylalanine triethanolamine, sodium myristoyl methylalanine, sodium lauroyl methyltaurine, potassium coconut oil fatty acid methyltaurine, sodium coconut oil fatty acid methyltaurine, magnesium coconut oil fatty acid methyltaurine, sodium myristoyl methyltaurine, sodium palmitoyl methyltaurine, sodium stearoyl methyltaurine, sodium oleoyl methyltaurine, sodium alkane sulfonate, sodium tetradecene sulfonate, sodium dioctyl sulfosuccinate, disodium lauryl sulfosuccinate, sodium coconut oil fatty acid ethyl ester sulfonate, sodium lauryl sulfate, triethanolamine lauryl sulfate, sodium cetyl sulfate, triethanolamine alkyl (11, 13,15) sulfate, sodium alkyl (12,13) sulfate, triethanolamine alkyl (12,13) sulfate, alkyl (12,14,16) ammonium sulfate, diethanolamine alkyl (12 to 13) sulfate, triethanolamine alkyl (12 to 14) sulfate, triethanolamine alkyl (12 to 15) sulfate, magnesium coconut oil alkyl sulfate/triethanolamine, ammonium lauryl sulfate, potassium lauryl sulfate, magnesium lauryl sulfate, monoethanolamine lauryl sulfate, diethanolamine lauryl sulfate, sodium myristyl sulfate, sodium steary lsulfate, sodium oleyl sulfate, triethanolamine oleyl sulfate, sodium polyoxyethylene lauryl ether sulfate, triethanolamine polyoxyethylene lauryl ether sulfate, sodium polyoxyethylene (1) alkyl (11,13,15) ether sulfate, triethanolamine polyoxyethylene (1) alkyl (11,13,15) ether sulfate, sodium polyoxyethylene (3) alkyl (11 to 15) ether sulfate, sodium polyoxyethylene (2) alkyl (12,13) ether sulfate, sodium polyoxyethylene (3) alkyl (12 to 14) ether sulfate, sodium polyoxyethylene (3) alkyl (12 to 15) ether sulfate, sodium polyoxyethylene (2) lauryl ether sulfate, sodium polyoxyethylene (3) myristyl ether sulfate, sodium higher fatty acid alkanol amide sulfate ester, lauryl phosphate, sodium lauryl phosphate, potassium cetyl phosphate, diethanolamine cetyl phosphate, polyoxyethylene oleyl ether phosphate, polyoxyethylene lauryl ether phosphate, sodium polyoxyethylene lauryl ether phosphate, polyoxyethylene cetyl ether phosphate, sodium polyoxyethylene cetyl ether phosphate, polyoxyethylene stearyl ether phosphate, polyoxyethylene oleyl ether phosphate, sodium polyoxyethylene oleyl ether phosphate, polyoxyethylene alkylphenyl ether phosphate, sodium polyoxyethylene alkylphenyl ether phosphate, triethanolamine polyoxyethylene alkylphenyl ether phosphate, polyoxyethylene octyl ether phosphate, polyoxyethylene (10) alkyl (12, 13) ether phosphate, polyoxyethylene alkyl (12 to 15) ether phosphate, polyoxyethylene alkyl (12 to 16) ether phosphate, triethanolamine polyoxyethylene lauryl ether phosphate and diethanolamine polyoxyethylene oleyl ether phosphate;

cationic surfactants, such as dioctylamine, dimethylstearylamine, trilaurylamine, diethylaminoethylamide stearate, lauryl trimethylammonium chloride, cetyl trimethylammonium chloride, cetyl trimethylammonium bromide, cetyl trimethylammonium saccharin, stearyl trimethylammonium chloride, alkyl (20 to 22) trimethylammonium chloride, lauryl trimethylammonium bromide, alkyl (16,18) trimethylammonium chloride, stearyl trimethylammonium bromide, stearyl trimethylammonium saccharin, alkyl (28) trimethylammonium chloride, di(polyoxyethylene)oleyl methylammonium (2EO) chloride, dipolyoxyethylene stearyl methylammonium chloride, polyoxyethylene (1) polyoxypropylene (25) diethylmethylammonium chloride, tri(polyoxyethylene) stearyl ammonium (5EO) chloride, distearyl dimethylammonium chloride, dialkyl (12 to 15) dimethylammonium chloride, dialkyl (12 to 18) dimethylammonium chloride, dialkyl (14 to 18) dimethylammonium chloride, dicocoyl dimethylammonium chloride, dicetyl dimethylammonium chloride, isostearyllauryl dimethylammonium chloride, benzalkonium chloride, myristyl dimethylbenzyl ammonium chloride, lauryl dimethyl (ethylbenzyl) ammonium chloride, stearyl dimethylbenzyl ammonium chloride, lauryl pyridinium chloride, cetyl pyridinium chloride, lauroyl cholamino formylmethylpyridinium chloride, stearoyl cholamino formylmethylpyridinium chloride, alkyl isoquinolinium bromide, methyl benzethonium chloride and benzethonium chloride;

ampholytic surfactants, such as 2-alkyl-N-carboxymethyl-N-hydroxyethyl imidazolium betaine, alkyldiamino ethyl glycine hydrochloride, sodium lauryldiamino ethyl glycine, sodium undecyl hydroxyethyl imidazolium betaine, undecyl-N-carboxymethyl imidazolium betaine, disodium coconut oil fatty acid acyl-N-carboxyethyl-N-hydroxyethyl ethylenediamine, disodium coconut oil fatty acid acyl-N-carboxyethoxyethyl-N-carboxyethyl ethylenediamine, disodium coconut oil fatty acid acyl-N-carboxymethoxyethyl-N-carboxymethyl ethylenediamine, sodium laurylamino propionate, sodium laurylamino dipropionate, triethanolamine laurylamino propionate, sodium palm oil fatty acid acyl-N-carboxyethyl-N-hydroxyethyl ethylenediamine, betaine lauryldimethylamino acetate, betaine coconut oil alkyldimethylamino acetate, betaine stearyl dimethylamino acetate, sodium stearyldimethyl betaine, coconut oil fatty acid amidopropyl betaine, palm oil fatty acid amidopropyl betaine, amidopropyl acetate betaine laurate, amidopropyl betaine ricinoleate, stearyl dihydroxyethyl betaine and lauryl hydroxysulfobetaine;

nonionic surfactants, such as polyoxyethylene (10) alkyl (12,13) ether, polyoxyethylene lauryl ether, polyoxyethylene cetyl ether, polyoxyethylene stearyl ether, polyoxyethylene oleyl ether, polyoxyethylene (3,7,12) alkyl (12 to 14) ether, polyoxyethylene tridecyl ether, polyoxyethylene myristyl ether, polyoxyethylene-sec-alkyl (14) ether, polyoxyethylene isocetyl ether, polyoxyethylene cetostearyl ether, polyoxyethylene (2,10,20) isostearyl ether, polyoxyethylene oleylcetyl ether, polyoxyethylene (20) arachyl ether, polyoxyethylene octyldodecyl ether, polyoxyethylene behenyl ether, polyoxyethylene octylphenyl ether, polyoxyethylene nonylphenyl ether, polyoxyethylene dinonylphenyl ether, polyoxyethylene (1) polyoxypropylene (1,2,4,8) cetyl ether, polyoxyethylene (5) polyoxypropylene (1,2,4,8) cetyl ether, polyoxyethylene (10) polyoxypropylene (1,2,4,8) cetyl ether, polyoxyethylene (20) polyoxypropylene (1,2,4,8) cetyl ether, polyoxyethylene polyoxypropylene lauryl ether, polyoxyethylene (3) polyoxypropylene (34) stearyl ether, polyoxyethylene (4) polyoxypropylene (30) stearyl ether, polyoxyethylene (34) polyoxypropylene (23) stearyl ether, polyoxyethylene polyoxypropylene cetyl ether, polyoxyethylene polyoxypropylene decyltetradecyl ether, polyethylene glycol monolaurate, ethylene glycol monostearate, polyethylene glycol monostearate, polyethylene glycol monooleate, ethylene glycol fatty acid ester, self-emulsifying ethylene glycol monostearate, diethylene glycol laurate, polyethylene glycol myristate, polyethylene glycol palmitate, diethylene glycol stearate, self-emulsifying polyethylene glycol (2) monostearate, polyethylene glycol isostearate, ethylene glycol dioctanoate, diethylene glycol dilaurate, polyethylene glycol dilaurate, polyethylene glycol (150) dipalmitate, ethylene glycol distearate, diethylene glycol distearate, polyethylene glycol distearate, ethylene glycol dioleate, polyethylene glycol dioleate, polyethylene glycol diricinoleate, polyoxyethylene (20) sorbitan monolaurate, polyoxyethylene (20) sorbitanmonopalmitate, polyoxyethylene (6) sorbitan monostearate, polyoxyethylene (20) sorbitan monostearate, polyoxyethylene (20) sorbitan tristearate, polyoxyethylene (6) sorbitan monooleate, polyoxyethylene (20) sorbitan monooleate, polyoxyethylene (20) sorbitan trioleate, polyoxyethylene (20) coconut oil fatty acid sorbitan, polyoxyethylene (10 to 80) sorbitan monolaurate, polyoxyethylene sorbitan tristearate, polyoxyethylene (20) sorbitan isostearate, polyoxyethylene (150) sorbitan tristearate, polyoxyethylene castor oil, polyoxyethylene hydrogenated castor oil, polyoxyethylene (10) hydrogenated castor oil, polyoxyethylene (20) hydrogenated castor oil, polyoxyethylene (40) hydrogenated castor oil, polyoxyethylene (50) hydrogenated castor oil, polyoxyethylene (60) hydrogenated castor oil, monomyristate glyceryl monoisostearate, glyceryl sesquioleate, glyceryl distearate, glyceryl diisostearate, glyceryl diarachidate, sorbitan monolaurate, sorbitan monopalmitate, sorbitan monostearate, sorbitan monoisostearate, sorbitan monooleate, sorbitan sesquistearate, sorbitan sesquioleate, sorbitan tristearate, sorbitan trioleate, coconut oil fatty acid sorbitan, sorbitan isostearate, sorbitan sesquiisostearate, sorbitan distearate, glyceryl caprylate, glyceryl caprinate, glyceryl laurate, glyceryl myristate, glyceryl stearate, glyceryl linoleate, glyceryl olerate, glyceryl isostearate, glyceryl behenate, glyceryl erucate, coconut oil fatty acid glyceryl, glyceryl ricinoleate, glyceryl hydroxystearate, wheat germ oil fatty acid monoglyceride, safflower oil fatty acid monoglyceride, hydrogenated soybean fatty acid monoglyceride, saturated fatty acid monoglyceride, cotton seed oil fatty acid monoglyceride, tallowate monoglyceride, lanolin fatty acid monoglyceride, sucrose fatty acid ester, coconut oil fatty acid sucrose ester, alkyl glucoxide, coconut oil alkyl dimethylamine oxide, lauryl dimethylamine oxide, dihydroxyethyl lauryl dimethylamine oxide, stearyl dimethylamine oxide, oleyl dimethylamine oxide, polyoxyethylene coconut oil alkyl dimethylamine oxide, polyglyceryl-3 caprylate, polyglyceryl-3 caprinate, polyglyceryl-3 laurate, polyglyceryl-4 laurate, polyglyceryl-6 laurate, polyglyceryl-10 laurate, polyglyceryl-6 myristate, polyglyceryl-10 myristate, polyglyceryl-6 palmitate, polyglyceryl-10 palmitate, polyglyceryl-2 isopalmitate, polyglyceryl-2 stearate, polyglyceryl-10 stearate, polyglyceryl-2 isostearate, polyglyceryl-10 isostearate, polyglyceryl-2 sesquioleate, polyglyceryl-6 distearate, polyglyceryl-10 distearate, polyglyceryl-2 diisostearate, polyglyceryl-10 diisostearate, polyglyceryl-2 triisostearate, polyglyceryl-10 tristearate, polyglyceryl-10 trioleate, polyglyceryl-2 tetraisostearate, polyglyceryl-10 pentastearate, polyglyceryl-6 pentaoleate, polyglyceryl-10 pentaoleate, polyglyceryl-10 heptastearate, polyglyceryl-10 decastearate, polyglyceryl-10 decaoleate and condensed polyglyceryl-6 ricinoleate;

natural surfactants, such as saponin, lecithin, soybean phospholipid, hydrogenated soybean phospholipid, soybean lysophospholipid, hydrogenated soybean lysophospholipid, yolk lecithin, hydrogenated yolk lysophosphatidylcholine, phosphatidylcholine, phosphatidylethanolamine, phosphatidylserine, sphingophospholipid, sphingomyelin, ganglioside, bile acid, cholic acid, deoxycholic acid, sodium cholate, sodium deoxycholate, spiculisporic acid, rhamnolipid, trehalose lipid, sophorolipid and mannosyl erythritol lipid;

ultraviolet ray absorbers such as: para-aminobenzoic acid derivatives, such as para-aminobenzoic acid, ethyl para-aminobenzoate, glyceryl para-aminobenzoate, amyl para-dimethyl aminobenzoate and 2-ethylhexyl para-dimethyl aminobenzoate, cinnamic acid derivatives, such as benzyl cinnamate, mono-2-ethyl hexanoate glyceryl dipara-methoxycinnamate, methyl 2,4-diisopropyl cinnamate, ethyl 2,4-diisopropyl cinnamate, potassium para-methoxycinnamate, sodium para-methoxycinnamate, isopropyl para-methoxycinnamate, 2-ethylhexyl para-methoxycinnamate, 2-ethoxyethyl para-methoxycinnamate and ethyl para-ethoxycinnamate, urocanic acid derivatives, such as urocanic acid and ethyl urocanate, benzophenone derivatives, such as 2,4-dihydroxybenzophenone, 2,2', 4,4'-tetrahydroxybenzophenone, sodium 2-hydroxy-4-methoxy-5-sulfobenzophenone, 2-hydroxy-4-methoxybenzophenone-5-sulfonate, 2-hydroxy-4-methoxybenzophenone, 2,2'-dihydroxy-4,4'-dimethoxybenzophenone and sodium 2,2'-dihydroxy-4,4'-dimethoxy-5-sulfobenzophenone, salicylic acid derivatives, such as ethylene glycol salicylate, salicylate-2-ethylhexyl, phenyl salicylate, benzyl salicylate, p-tert-butylphenyl salicylate, homomethyl salicylate and salicylate-3,3,5-trimethylcyclohexyl, and 2-(2'-hydroxy-5'-methoxyphenyl)benzotriazole and 4-tert-butyl-4'-methoxybenzoyl methane;

powders and color materials such as: kaolin, silicic anhydride, magnesium aluminum silicate, sericite, talc, boron nitride, mica, montmorillonite, hemp cellulose powder, wheat starch, silk powder, maize starch; natural dyes, such as nitro dyes, azo dyes, nitroso dyes, triphenylmethane dyes, xanthene dyes, quinoline dyes, anthraquinone dyes, indigo dyes, pyrene dyes, phthalocyanine dyes, flavonoid, quinone, porphyrin, water soluble annatto, sepia powder, caramel, guaiazulene, gardenia blue, gardenia yellow, cochineal, shikonin, sodium copper chlorophyllin, paprika dye, safflower red, safflower yellow, laccaic acid and riboflavin butyrate ester; carbon black, yellow iron oxide, black iron oxide, red iron oxide, iron blue, ultramarine blue, zinc oxide, chromium oxide, titanium oxide, black titanium oxide, zirconium oxide, chromium hydroxide, alumina, magnesium oxide, barium sulfate, aluminum hydroxide, calcium carbonate, lithium cobalt titanate, manganese violet and pearl pigment;

plant extracts, such as *Angelica keiskei* extract, *Uncaria gambir* extract, avocado extract, sweet hydrangea leaf extract, *Gynostemma pentaphyllum* makino extract, *Althaea officinalis* extract, *Arnica montana* extract, oil soluble *Arnica montana* extract, almond extract, aloe extract, Japanese *styrax benzoin* extract, *Ginkgo biloba* extract, Stinging nettle extract, Orris rhizome root extract, fennel extract, turmeric extract, dog rose fruit extract, Echinacea leaf extract, *Scutellaria* root extract, Phellodendron bark extract, Japanese captis extract, barley extract, okura extract, *Hypericum perforatum* extract, oil soluble *Hypericum perforatum* extract, *Lamium album* extract, oil soluble *Lamium album* extract, *Ononis spinosa* root extract, *Nasturtium officinale* extract, orange extract, orange flower water, seaweed extract, persimmon tannin, pueraria root extract, Japanese valerian extract, cattail extract, Chamomile (matricaria) extract, oil soluble Chamomile (matricaria) extract, Chamomile (matricaria) distillate, *Avena sativa* (oat) kernel extract, carrot extract, oil soluble carrot extract, carrot oil, *Artemisia capillaris* extract, *Glycyrrhiza glabra* (licorice) extract, powdered *Glycyrrhiza glabra* (licorice) extract, *Glycyrrhiza glabra* (licorice) extract flavonoid, cantharides tincture, raspberry extract, kiwi extract, cinchona extract, cucumber extract, apricot kernel extract, quince seed extract, gardenia florida extract, *Sasa albomarginata* extract, *Sophora* root extract, walnut shell extract, *Citrus paradisi* (grapefruit) extract, *Clematis vitalba* leaf extract, black sugar extract, *chlorella* extract, mulberry bark extract, Cinnamon bark extract, Gentian extract, Geranium herb extract, black tea extract, Nuphar extract, burdock root extract, oil soluble burdock root extract, wheat germ extract, hydrolyzed wheat powder, rice bran extract, fermented rice bran extract, *Symphytum officinale* (comfrey) extract, *Asiasarum* root extract, *Crocus sativus* (saffron) extract, *Saponaria officinalis* extract, oil soluble salvia extract, *Crataegus cuneata* fruit extract, *Zanthoxylum* fruit extract, *Lentinus edodes* extract, powdered *Lentinus edodes* extract, *Rehmannia* root extract, *Lithospermum* root extract, oil soluble *Lithospermum* root extract, *Perilla* herb extract, linden extract, oil soluble *Tilia europaea* extract, *Filipendula* extract, Peony root extract, *Coix lacryma-jobi* extract, ginger extract, oil soluble ginger extract, ginger tincture, *Acorus calamus* root extract, *Betula pendula* (birch) extract, oil soluble *Betula alba* (birch) extract, *Betula pendula* (birch) sap, *Lonicera japonica* extract, *Equisetum arvense* extract, oil soluble *Equisetum arvense* extract, scordinin, stevia extract, ivy extract, *Crataegus oxyacantaha* (whitethorn) extract, *sambucus* extract, *Juniperus communis* extract, *Achillea milefolium* extract, oil soluble *Achillea milefolium* extract, *Mentha piperita* (peppermint) extract, *Salvia officinalis* (sage) extract, oil soluble *Salvia officinalis* (sage) extract, *Salvia officinalis* (sage) water, *Malva Sylvestris* (mallow) extract, *Apium graveolens* (celery) extract, *Cnidium officinale* extract, *Cnidium officinale* water, *Swertia* herb extract, *Glycine max* (soybean) extract, Jujube extract, thyme extract, green tea extract, tea leaf dry distilled solution, tea seed extract, clove extract, *Citrus unshiu* peel extract, *Camellia japonica* extract, *Centella asiatica* extract, oil soluble walnut extract, duku extract, *Terminalia sericea* extract, *Capsicum* tincture, Japanese angelica root extract, oil soluble Japanese angelica root extract, Japanese angelica root water, *Calendula officinalis* flower extract, oil soluble *Calendula officinalis* flower extract, soy milk powder, peach seed extract, Bitter orange peel extract, *Houttuynia cordata* extract, *Solanum lycopersicum* (tomato) extract, *Potentilla tormentilla* Schrk (Rosaceae) extract, fermented soybeans extract, Ginseng extract, oil soluble Ginseng extract, *Allium sativum* (garlic) extract, wild rose extract, oil soluble wild rose extract, malt extract, malt root extract, Ophiopogon tuber extract, parsley extract, rye leaf juice concentrate, peppermint distillate, witch hazel distillate, witch hazel extract, rose extract, *parietaria* extract, *Isodonis japonicus* extract, *Eriobotrya japonica* leaf extract, oil soluble *Eriobotrya japonica* leaf extract, coltsfoot extract, hoelen extract, *Ruscus aculeatus* root extract, powdered *Ruscus aculeatus* root extract, grape extract, grape leaf extract, grape water, Hayflower extract, *Luffa cylindrica* fruit extract, *Luffa cylindrica* fruit water, *Carthamus tinctorius* (safflower) extract, oil soluble *Tilia platyphyllos* extract, linden distillate, *Paeonia suffruticosa* (peony) extract, *Humulus lupulus* (hops) extract, oil soluble *Humulus lupulus* (hops) extract, pine extract, *Silybum marianum* (milk thistle) extract, *Aesculus hippocastanum* (horse chestnut) extract, oil soluble *Aesculus hippocastanum* (horse chestnut) extract, *Sapindus mukurossi* extract, *Melissa officinalis* (balm mint) extract, *Melilotus officinalis* (melilot) extract, *Prunus persica* (peach) leaf extract, oil soluble *Prunus persica* (peach) leaf extract, bean sprouts extract, *Centaurea cyanus* flower extract, *Centaurea cyanus* flower distillate, *Eucalyptus globulus* extract, Saxifrage extract, *Lilium* (lily) extract, *Coix* seed extract, oil soluble *Coix* seed extract, *Artemisia princeps pampanini* extract, *Artemisia princeps pampanini* water, *Lavandula angustifolia* (lavender) extract, *Lavandula ngustifolia* (lavender) water, apple extract, *Ganoderma lucidum extract*, *Lactuca sativa* (lettuce) extract, lemon extract, *Astragalus sinicus* extract, *Rosa centifolia* (rose) flower water, *Rosemarinus officinalis* (rosemary) extract, oil soluble *Rosemarinus officinalis* (rosemary) extract, *Anthemis nobilis* extract and *Sanguisorba officinalis* extract;

amino acids and peptides, such as glycine, alanine, valine, leucine, isoleucine, serine, threonine, phenylalanine, tyrosine, tryptophan, cystine, cysteine, methionine, proline, hydroxyproline, aspartic acid, asparagine, glutamic acid, glutamine, arginine, histidine, lysine, γ-aminobutyric acid, DL-pyrrolidonecarboxylic acid, ε-aminocaproic acid, hydrolyzed elastin, water soluble elastin, hydrolyzed collagen, water soluble collagen, casein, glutathione, wheat peptides and soybean peptide;

vitamins and factors acting like a vitamin such as: vitamin A and analogues thereof, such as retinol, retinal, retinoic acid, retinol acetate and retinol palmitate; carotenoids, such as α-carotene, β-carotene, γ-carotene, δ-carotene, lycopene, zeaxanthin, cryptoxanthin, echinenon and astaxanthin; vitamin $B_1$ and analogues thereof, such as thiamines; vitamin $B_2$ and analogues thereof, such as riboflavin; vitamin $B_6$ and analogues thereof, such as pyridoxine, pyridoxal and pyridoxamine; vitamin $B_{12}$ and analogues thereof, such as cyanocobalamin; folic acids, nicotinic acid, nicotinamide, pantothenic acids, biotins; vitamin C and analogues thereof, such as L-ascorbic acid, sodium L-ascorbate, L-ascorbyl stearate, L-ascorbyl palmitate, L-ascorbyl dipalmitate, L-ascorbyl tetraisopalmitate, L-ascorbate sulfate disodium ester, magnesium L-ascorbyl, sodium L-ascorbyl phosphate and L-ascorbate-2-glucoside; vitamin D and analogues thereof, such as ergocalciferol and cholecalciferol; vitamin E and analogues thereof, such as d-α-tocopherol, DL-α-tocopherol, dl-α-tocopherol acetate, dl-α-tocopherol succinate, β-tocopherol, γ-tocopherol and d-δ-tocopherol; ubiquinones, vitamin K and analogues thereof, carnitine, ferulic acid, γ-oryzanol, α-lipoic acid and orotic acid;

antiseptic agents, such as benzoic acid, sodium benzoate, undecylenicacid, salicylic acid, sorbic acid, potassiumsorbate, dehydroacetic acid, sodium dehydroacetate, isobutyl parahydroxybenzoate, isopropyl parahydroxybenzoate, ethyl parahydroxybenzoate, butyl parahydroxybenzoate, propyl parahydroxybenzoate, benzyl parahydroxybenzoate, methyl parahydroxybenzoate, sodium parahydroxybenzoate methyl, phenoxyethanol, light sensitive dye No. 101, light sensitive dye No. 201 and light sensitive dye No. 401;

antioxidizing agents, such as butylhydroxyanisole, butylhydroxytoluene, propyl gallate, erythorbic acid, sodium erythorbate, para-hydroxyanisole and octyl gallate;

chelating agents to bind to a metal ion, such as trisodium ethylenediamine hydroxyethyl triacetate, edetic acid, disodium edetate, trisodium edetate, tetrasodium edetate, sodium citrate, gluconic acid, phytic acid, sodium polyphosphate and sodium metaphosphate;

moisturizing agents, such as hyaluronic acid, sodium hyaluronate, sodium chondroitin sulfate, sodium lactate, sodium pyrrolidone carboxylate, betaine, lactic acid bacteria fermented solution, yeast extract and ceramide;

anti-inflammatory agents, such as glycyrrhizic acid, trisodium glycyrrhizinate, dipotassium glycyrrhizinate, monoammonium glycyrrhizinate, β-glycyrrhetinic acid, glycerin glycyrrhetinate, stearyl glycyrrhetinate, lysozyme chloride, hydrocortisone and allantoin;

pH adjusting agents, such as sodium hydroxide, potassium hydroxide and triethanolamine;

salts, such as sodium chloride, potassium chloride, magnesium chloride and sodium sulfate;

α-hydroxy acids, such as citric acid, glycolic acid, tartaric acid and lactic acid;

whitening agents such as arbutin, α-arbutin and placenta extract;

essential oils, such as *Archangelica officinalis* (angelica) oil, *Canangium odoratum* (ylang ylang) oil, *Canarium luzonicum* (elemi) oil, orange oil, *Chamomilla recutita* (matricaria) oil, *Anthemis nobilis* oil, *Elettaria cardamom* (cardamon) oil, *Acorus calamus* (calamus) oil, *Ferula galbaniflua* (galbanum) oil, *Cinnamomum camphora* (camphor) oil, *Daucus carota* (carrot) seed oil, *Salvia sclarea* (clarysage) oil, *Citrus paradisi* (grapefruit) oil, *Eugenia caryophyllus* (clove) oil, Cinnamon bark oil, *Coriandrum sativum* (coriander) oil, *Cupressus sempervirens* (cypress) oil, *Santalum album* (sandalwood) oil, *Juniperus virginiana* (cedarwood) oil, *Cympogon nardus* (citronella) oil, *Cinnamomum zeylanicum* (Cinnamon) leaf oil, *Jasmine officinale* (jasmine) absolute oil, *Juniperus communis* (juniper Berry) oil, *Zingiber officinale* (ginger) extract, *Mentha spicata* (spearmint) oil, *Salvia officinalis* (sage) oil, cedar oil, *Pelargonium grabeolens* (geranium) oil, *Thymus vulgaris* (thyme) oil, *Melaleuca alternifolia* (tea tree) oil, *Myristica fragrans* (nutmeg) oil, *Melaleuca quiviridiflara* (niaouli) oil, *Citrus aurantium* (neroli) oil, pine oil, *Ocimum basilicum* (basil) oil, *Mentha arvensis* oil, *Pogostemon patchouli* (patchouli) oil, *Cymbopogon martini* (palmarosa) oil, *Foeniculum vulgare* (fennel) oil, *Citrus bigaradia* (petitgrain) oil, *Piper nigrum* (black pepper) oil, *Boswellia carterii* (frankincense) oil, *Vetiveria zizanoides* (vetivert) oil, *Mentha piperita* (peppermint) oil, *Citrus bergamia* (bergamot) oil, benzoin oil, *Aniba rosaeodora* (bois de rose) oil, *Origanum majorana* (marjoram) oil, mandarin oil, *Conumiphora myrrha* (myrrh) oil, *Melissa officinalis* (balm mint) oil, *Eucalyptus globulus* oil, *Citrus junos* oil, *Citrus aurantifolia* (lime) oil, *Ravensare aromaticum* (ravensare) oil, *Lavandula latifolia* (lavandin) oil, *Lavandula angustifolia* (lavender) oil, *Tilia vulgaris* (linden) oil, lemon oil, lemon grass oil, rose oil, *Aniba rosaeodora* (rosewood) oil, *Rosemarinus officinalis* (rosemary) oil and *Levisticum officinale* (lovage) oil;

terpenes, such as limonene, pinene, terpinene, terpinolene, myrcene and longifeelene;

fragrance; and water.

[Skin External Preparation, Cosmetics]

Use of the emulsion composition of the invention is not specifically restricted, and the emulsion composition can be preferably used for, for example, skin external preparations. In particular, the emulsion composition can be preferably used for cosmetics that are most embodiments of the skin external preparations. The cosmetic of the invention is not specifically restricted provided that it is brought into contact with the skin when used, and can be widely used for a lotion, a beauty liquid, a gel and the like. Further, the cosmetic of the invention is employable irrespective of age or sex of users.

To the cosmetic of the invention, the existing raw materials of cosmetics may be further added within limits not detrimental to the effects of the invention.

As the existing raw materials of cosmetics, there can be mentioned those described in, for example, Keshouhin genryo kizyun (Standards of raw materials of cosmetics), second edition, notes, edited by Society of Japanese Pharmacopoeia, 1984 (Yakuji Nippo Ltd.), Keshouhin genryo kizyun-gai seibun kikaku (Standards of raw materials of cosmetics, non-standard ingredients), under the editorship of Pharmaceutical Affairs Bureau Evaluation and Registration Division, 1993 (Yakuji Nippo Ltd.), Keshouhin genryo kizyun-gai seibun kikaku tsuiho (Standards of raw materials of cosmetics, non-standard ingredients, Supplement), under the editorship of Pharmaceutical Affairs Bureau Evaluation and Registration Division, 1993 (Yakuji Nippo Ltd.), Keshouhin syubetsu kyoka kizyun (Standards of cosmetic classification permission), under the editorship of Pharmaceutical Affairs Bureau Evaluation and Registration Division, 1993 (Yakuji Nippo Ltd.), Keshouhin syubetsu haigou seibun kikaku (Standards of cosmetic classification ingredients), under the editorship of Pharmaceutical Affairs Bureau Evaluation and Registration Division, 1997 (Yakuji Nippo Ltd.), Keshouhin genryou jiten (Dictionary of raw materials of cosmetics), 1991 (Nikko Chemicals Co., Ltd.), etc.

The skin external preparation and the cosmetic of the invention can be prepared by blending the above components so that the given contents should be obtained and then dissolving, mixing or dispersing them by a conventional method according to an embodiment of the agent or the cosmetic.

[Method for Stabilizing Skin External Preparation Containing Salt of Ascorbic Acid Ester]

As described hereinbefore, by preparing an emulsion composition containing the salt of ascorbic acid ester (A) and having a transparent to translucent appearance, decrease of the salt of ascorbic acid ester (A) attributable to decomposition of the salt can be inhibited even when the salt of ascorbic acid ester (A) is used to prepare a skin external preparation.

That is to say, by preparing a fine emulsion composition containing the salt of ascorbic acid ester (A) and having a transparent to translucent appearance, a method for stabilizing a skin external preparation containing the salt of ascorbic acid ester (A) can be provided. Such a method for stabilizing a skin external preparation containing the salt of ascorbic acid ester (A) is also a part of the present invention.

EXAMPLES

The present invention is further described with reference to the following examples, but it should be construed that the invention is in no way limited to those examples. In the following examples, glycerin having a glycerin content of not less than 98% by mass was used as glycerin. The unit of each numerical value in the tables is % by mass. The evaluation methods used in the examples are shown below.

<Mean Particle Diameter>

A mean particle diameter of an agent prepared was measured by the use of a particle size distribution measuring device ("Nanotrack UPA-EX150" manufactured by Nikkiso Co., Ltd.). An agent having a mean particle diameter of not more than 100 nm was evaluated as "AA", an agent having a mean particle diameter of more than 100 nm and not more than 200 nm was evaluated as "BB", an agent having a mean particle diameter of more than 200 nm and not more than 500 nm was evaluated as "CC", and an agent having a mean particle diameter of more than 500 nm was evaluated as "DD".

<Appearance>

An agent prepared was placed in a transparent cell having a cell length of 5 mm, and whether letters of a newspaper placed on the other side of the cell were distinguishable through the cell was confirmed by visual observation. An agent in the cell through which the letters were clearly distinguishable was evaluated as "AA", an agent in the cell through which the letters were distinguishable was evaluated as "BB", and an agent in the cell through which the letters were indistinguishable was evaluated as "CC".

<Storage Stability Test>

An agent prepared was allowed to stand still at a temperature of 40° C. for 2 months, and then a remaining ratio (%) of the salt of ascorbic acid ester (A) was calculated from the following formula. An agent having a remaining ratio of not less than 80% was evaluated as "AA", and an agent having a remaining ratio of less than 80% was evaluated as "BB".

Remaining ratio (%)=100×[concentration (%) of component (A) after allowed to stand/concentration (%) of component (A) immediately after preparation]

The concentration of the component (A) was measured by means of high-performance liquid chromatography under the following measuring conditions.

<High-Performance Liquid Chromatography Measuring Conditions>

Column: Shodex (trademark) C18P 4E, manufactured by Showa Denko K.K.
Column temperature: 40° C.
Eluate: 0.1M dipotassium hydrogenphosphate (pH 7.0)/tetrahydrofuran (65/35)
Flow rate: 0.7 ml/min
Detection: UV 265 nm Examples 1 to 4

Comparative Examples 1 to 8

The components (I) were mixed and dissolved at 80° C. in compositional proportions shown in Table 1 and Table 2, then to the components (I), the components (II) having been mixed and dissolved at 80° C. separately were added, and they were emulsified by cooling with stirring and then cooled to 30° C. to prepare emulsions. The emulsions thus prepared were subjected to the above evaluation. The results are set forth in Table 1 and Table 2.

TABLE 1

|   |   | Ex. 1 | Ex. 2 | Comp. Ex. 1 | Comp. Ex. 2 | Comp. Ex. 3 | Comp. Ex. 4 |
|---|---|---|---|---|---|---|---|
| I | Squalane | 2.0 | 2.0 |  | 2.0 | 2.0 | 2.0 |
|   | Isononyl isononanoate |  |  | 2.0 |  |  |  |
|   | Polyglyceryl-10 oleate | 1.35 | 1.35 | 1.35 | 1.8 | 0.5 |  |
|   | Polyglyceryl-2 oleate | 0.65 | 0.65 | 0.65 | 0.2 | 1.5 |  |
|   | Polyglyceryl-10 stearate |  |  |  |  |  | 1.35 |
|   | Polyglyceryl-2 stearate |  |  |  |  |  | 0.65 |
| II | Ascorbic acid-2-phosphoric acid-6-palmitic acid Na salt | 1.0 | 1.0 | 1.0 | 1.0 | 1.0 | 1.0 |
|   | Glycerin | 4.0 | 4.0 | 4.0 | 4.0 | 4.0 | 4.0 |
|   | 1,3-Butanediol | 4.0 |  | 4.0 |  | 4.0 | 4.0 |
|   | 1,2-Hexanediol |  | 4.0 |  | 4.0 |  |  |
|   | Purified water | the balance | the balance | the balance | the balance | the balance | the balance |
|   | Total | 100 | 100 | 100 | 100 | 100 | 100 |
|   | Remaining ratio | AA | AA | BB | BB | BB | BB |
|   | Particle diameter | AA | BB | CC | CC | CC | DD |
|   | Appearance | AA | BB | CC | CC | CC | CC |

TABLE 2

|   |   | Ex. 3 | Ex. 4 | Comp. Ex. 5 | Comp. Ex. 6 | Comp. Ex. 7 | Comp. Ex. 8 |
|---|---|---|---|---|---|---|---|
| I | Liquid paraffin | 2.0 | 2.0 |  | 10.0 | 0.1 | 2.0 |
|   | Trioctanoin |  |  | 2.0 |  |  |  |
|   | Polyglyceryl-10 oleate | 1.35 | 1.35 | 1.35 | 1.35 | 0.5 |  |
|   | Polyglyceryl-2 oleate | 0.65 | 0.65 | 0.65 | 0.65 | 1.5 |  |

TABLE 2-continued

|  |  | Ex. 3 | Ex. 4 | Comp. Ex. 5 | Comp. Ex. 6 | Comp. Ex. 7 | Comp. Ex. 8 |
|---|---|---|---|---|---|---|---|
|  | Polyglyceryl-10 stearate |  |  |  |  |  | 1.35 |
|  | Polyglyceryl-2 stearate |  |  |  |  |  | 0.65 |
| II | Ascorbic acid-2-phosphoric acid-6-hexyldecanoic acid Na salt | 1.0 | 1.0 | 1.0 | 1.0 | 1.0 | 1.0 |
|  | Glycerin | 4.0 | 4.0 | 4.0 | 4.0 | 4.0 | 4.0 |
|  | 1,3-Butanediol | 4.0 |  | 4.0 |  | 4.0 | 4.0 |
|  | 1,2-Hexanediol |  | 4.0 |  | 4.0 |  |  |
|  | Purified water | the balance | the balance | the balance | the balance | the balance | the balance |
|  | Total | 100 | 100 | 100 | 100 | 100 | 100 |
|  | Remaining ratio | AA | AA | BB | BB | BB | BB |
|  | Particle diameter | AA | BB | CC | CC | BB | DD |
|  | Appearance | AA | BB | CC | CC | BB | CC |

It is evident from Table 1 and Table 2 that in Examples 1 to 4, decrease of the component (A) was more inhibited as compared with that in Comparative Examples 1 to 8, and excellent storage stability was confirmed. Further, a transparent to translucent beautiful appearance was retained.

Transparency of preparations enhances the merchandise value of cosmetics, and an emulsion composition capable of retaining high storage stability with maintaining transparency over a long period of time has been accomplished by the present invention for the first time and is of extremely high industrial value.

The invention claimed is:

1. An emulsion composition comprising:
(A) a salt of a higher fatty acid ester of ascorbic acid-2-phosphoric acid ester, said higher fatty acid ester of ascorbic acid-2-phosphoric acid ester being represented by the following formula (1):

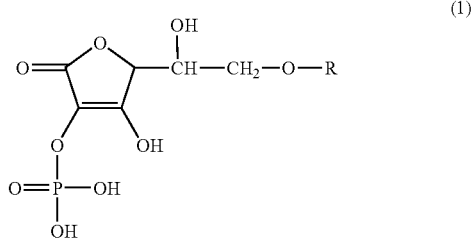

wherein R is a higher fatty acid residual group,
(B) polyglyceryl-10 oleate,
(C) polyglyceryl-2 oleate, and
(D) squalane or liquid paraffin,
wherein the blending ratio by mass between the component (B) and the component (C), (B):(C), is in the range of 1:1 to 3:1, and the blending ratio by mass between the total of the components (B) and (C) and the component (D), (B)+(C):(D), is in the range of 10:1 to 1:4.

2. The emulsion composition as claimed in claim 1, wherein R in the formula (1) is a residual group of an aliphatic carboxylic acid of 10 to 20 carbon atoms.

3. The emulsion composition as claimed in claim 2, wherein the aliphatic carboxylic acid is lauric acid, myristic acid, palmitic acid, stearic acid, 2-hexyldecanoic acid or isostearic acid.

4. The emulsion composition as claimed in claim 2, wherein the aliphatic carboxylic acid is palmitic acid.

5. The emulsion composition as claimed in claim 2, wherein the aliphatic carboxylic acid is 2-hexyldecanoic acid.

6. The emulsion composition as claimed in claim 1, wherein the component (A) is a Na salt, a K salt, a Mg salt or a Zn salt.

7. The emulsion composition as claimed in claim 1, wherein the content of the component (A) is in the range of 0.01 to 20% by mass.

8. The emulsion composition as claimed in claim 1, wherein the mean emulsion particle diameter is in the range of 1 nm to 200 nm.

9. A skin external preparation, comprising the emulsion composition of claim 1.

10. A cosmetic comprising the emulsion composition of claim 1.

11. A method for stabilizing the skin external preparation of claim 9, comprising preparing the emulsion according to claim 9 having a mean emulsion particle diameter of 1 nm to 200 nm by using, as emulsifying agents, (B) polyglyceryl-10 oleate and (C) polyglyeeryl-2 oleate.

* * * * *